(12) United States Patent
Miyazaki

(10) Patent No.: US 6,510,335 B1
(45) Date of Patent: Jan. 21, 2003

(54) VISUALIZATION OF NONENHANCED MR LYMPHOGRAPHY

(75) Inventor: Mitsue Miyazaki, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/513,078

(22) Filed: Feb. 25, 2000

(30) Foreign Application Priority Data

Feb. 26, 1999 (JP) .......................................... 11-051824

(51) Int. Cl.$^7$ .............................................. A61B 5/055
(52) U.S. Cl. ...................... 600/419; 600/410; 324/307; 324/309
(58) Field of Search ................................. 600/410, 418, 600/419; 324/307, 309

(56) References Cited

U.S. PATENT DOCUMENTS

| | | | |
|---|---|---|---|
| 4,694,837 A | * 9/1987 | Blakeley et al. | ............ 600/484 |
| 5,377,679 A | * 1/1995 | Machida et al. | ............ 600/422 |
| 5,422,576 A | * 6/1995 | Kao et al. | ................... 324/309 |
| 6,068,595 A | * 5/2000 | Miyazaki et al. | ............ 324/309 |
| 6,144,201 A | * 11/2000 | Miyazaki | ................... 324/306 |

OTHER PUBLICATIONS

M. Miyazaki et al., "A Novel MR Angiography Technique" SPEED Acquisition Using Half–Fourier RARE, J. Magnetic Resonance Imaging: 8: 505–507 (1998).

S. Hayashi et al., "Thoracic Duct: Visualization at Nonenhanced MR Lymphography–Initial Experience[1]", Radiology 1999; 212:598–600.

* cited by examiner

Primary Examiner—Marvin M. Lateef
Assistant Examiner—Runa Shah Qaderi
(74) Attorney, Agent, or Firm—Nixon & Vanderhye P.C.

(57) ABSTRACT

MR lymphography depicts lymph liquid that flows through lymphatic vessels and lymph nodes, such liquids can easily be depicted with no contrast agent. An effective echo time ($TE_{eff}$) of a pulse sequence is selected to depict the desired lymph liquid. The effective echo time is determined to be relatively long as compared to the T1 relaxation time of blood. For example, an effective echo time may be in the range of 120 to 800 msec when a pulse sequence is based on the FAST method. In this case, it is preferred that an echo train spacing (ETS) is relatively short, for example, ETS=3 to 10 msec. The pulse sequence is performed and an MR signal generated in response to the pulse sequence is acquired. From the MR signal, an image is produced wherein the lymph is highlighted while vessels providing a background are also depicted, although the contrast of the background vessel is kept lower than that of the highlighted lymph liquid.

20 Claims, 6 Drawing Sheets

VISUALIZATION OF NONENHANCED MR LYMPHOGRAPHY

BACKGROUND OF THE INVENTION

1. Technical Field of the Invention

The present invention relates to medical magnetic resonance imaging (MRI) for visualizing the inner body of an object to be diagnosed on a magnetic resonance phenomenon, in particular, to MR imaging capable of depicting such fluid as lymphatic vessels and lymph nodes which not only flow at slower speeds but also are thinner than blood vessels.

In this specification, imaging for lymphatic vessels and lymph nodes in accordance with the present invention is referred to as "MR Lymphography."

2. Description of Prior Art

Magnetic resonance imaging is based on a technique that magnetically excites nuclear spins of an object placed in a static magnetic field with an RF signal of a Larmor frequency thereof, acquires an MR signal emanated therefrom due to the excitation, and reconstructs an image using the MR signal.

In the field of MR imaging, there is provided MR angiography (MRA) for imaging blood vessels. At present, this MRA is accomplished by various techniques including a time of flight (TOF) method, a phase contrast (PC) method and a method of enhanced MR angiography with contrast agent.

As to thoracic duct flowing also in the body, no imaging method has been provided so far in the field of MRI, although lymph liquid appears to be similar to blood, due to the fact that the lymph liquid flows at slower speeds than blood through thinner ducts than blood vessels.

Conventionally, lymphatic vessels of an object are visualized on the X-ray Lymphography with contrast agent injected into the object. It is further reported that lymph nodes can be visualized by performing MR imaging with contrast agent injected into an object.

However, any conventional technique of imaging lymphatic vessels and lymph nodes requires injection of contrast agent. In general, it takes a long time (e.g., a few hours) to inject such contrast agent, which imposes heavy mental and physical burdens on a patient. It is frequently true that contrast agent is characteristically undesirable for a patient, resulting in imaging using contrast agent that can not provide a universal solution to lymphography. Thus, at present, it is the case that there is no imaging method permitting an easy diagnosis of lymphatic-system diseases.

SUMMARY OF THE INVENTION

The present invention has been performed in consideration of the drawbacks that the foregoing conventional imaging for lymphography faces. An object of the present invention is to easily depict lymph liquid that flows through lymphatic vessels and lymph nodes with no contrast agent.

In order to realize the above object, in an MRI system according to the present invention, by scanning means, a pulse sequence of an effective echo time ($TE_{eff}$) selected to depict desired fluid other than blood within an object is performed and an MR signal generated in response to the performance of the pulse sequence is acquired. And by producing means, an image wherein the fluid is highlighted is produced from the MR signal.

Thus, because the effective echo time is selected as a time that agrees with depiction of fluids (such as lymph liquid or liquid residing in recesses) with respect to the length of T1 time of blood, an MR image highlighting the fluid can be provided without using any contrast agent. This MR image is greatly useful to understand the flow and behavior of the liquid such as lymph liquid, making it useful to diagnose lymph system diseases.

It is preferred that the scanning means performs the pulse sequence toward the fluid which is made up of lymph liquid existing in a lymphatic vessel, which flows at a slower speed than the blood. It is also preferred that the effective echo time is selected to be long with respect to the T1 (spin-lattice relaxation) time (normally, 900 to 1000 msec) of the blood.

For example, the effective echo time is selected to be a relatively long time such that both the lymphatic vessel and a blood vessel existing around the lymph liquid are depicted together, the lymph vessel having priority over the blood vessel in contrast. By way of example, the pulse sequence is either a two-dimensional sequence or a three-dimensional sequence. It is possible that the pulse sequence is based on one of FSE (fast SE) method, FASE (Fast Asymmetric SE) method, EPI (Echo Planar Imaging) and fast recovery (FR) methods. The pulse sequence may be based on an FASE (Fast Asymmetric SE) method wherein echo train spacing (ETS) is selected to be a relatively short time. Preferably, the effective echo time $TE_{eff}$ is selected from a range of 120 to 800 msec and the echo train spacing ETS is selected from a range of 3 to 10 msec.

It is preferred that the pulse sequence is a three-dimensional sequence and the producing means produce three-dimensional image data using the echo signal and obtain the image by performing maximum intensity processing with the three-dimensional image data.

Preferably, the above main MR system configuration further comprises detecting means for detecting a signal indicative of a cardiac temporal phase of the object, the scanning means including scan start means for repetitively starting the pulse sequence synchronously with time delayed by a certain interval from a heartbeat-specific reference wave appearing in the signal. For instance, the certain interval delayed by the scan start means is selected from a range of 500 to 600 msec so as to acquire the echo signal at a diastole of a heart of the object.

In addition, the above main MR system configuration may further comprise instructing means for instructing the object to hold their breath during the trip a pulse sequence is performed by the scanning means. For example, the breath holding may be instructed based on an intermittent breath-holding method.

Still further, in the above main MR system, the fluid may be liquid filled in a concavity within the object.

On the other hand, an MR imaging method of the present invention comprises the steps of: not merely performing a pulse sequence of echo time ($TE_{eff}$) selected to depict desired fluid other than blood within an object but also acquiring an MR signal generated in response to the performance of the pulse sequence, and producing from the MR signal an image wherein the fluid is highlighted. Thus, an MR image highlighting the fluid can be provided without using any contrast agent.

DETAILED DESCRIPTION OF THE PREFERRED EMBODIMENTS

Hereafter, with reference to FIGS. 1 to 7, an embodiment of the present invention will be described.

Figure 1:
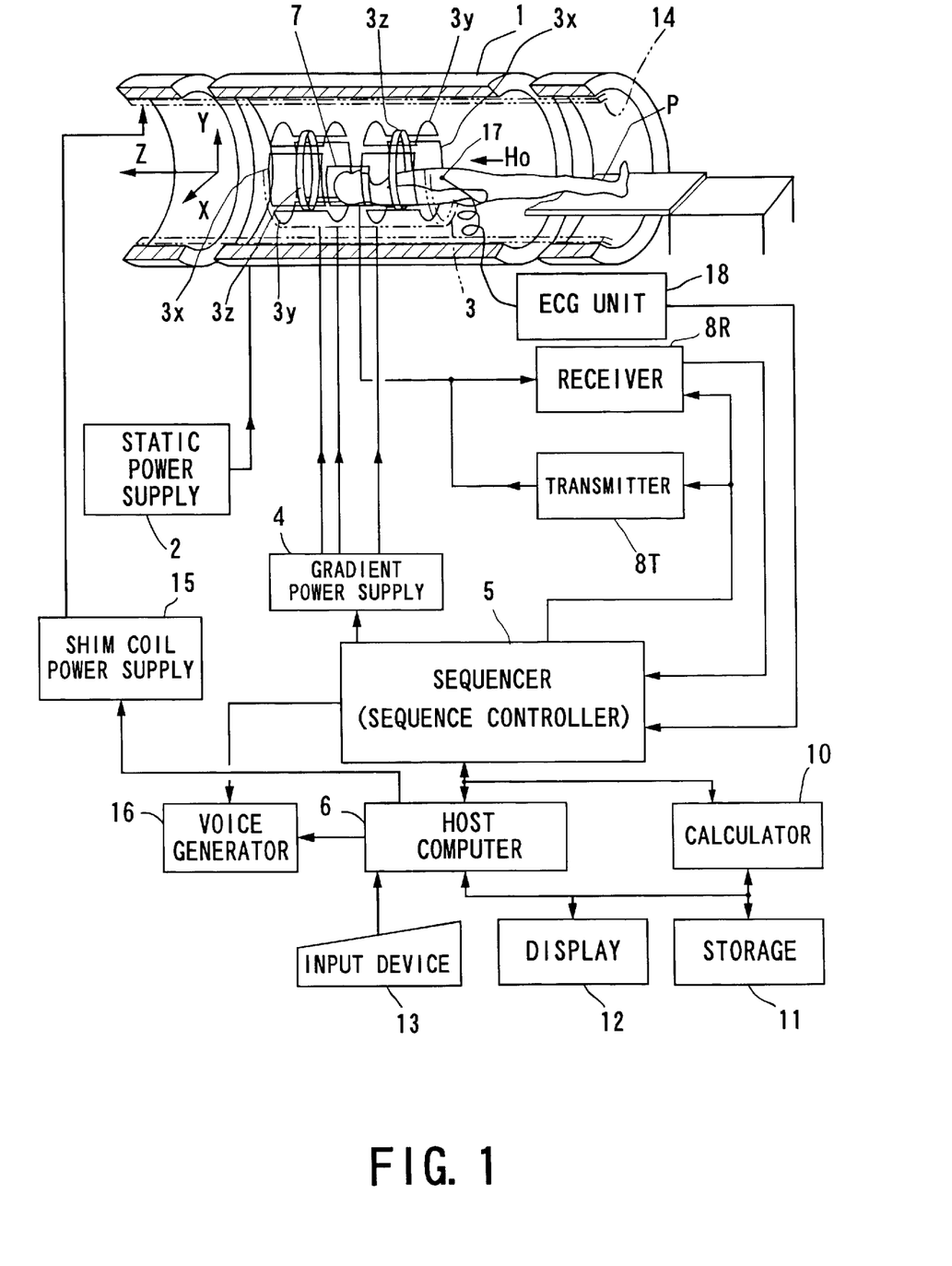
FIG. 1 functionally shows a block diagram of one constructional example of an MRI system according to the present invention.

Firstly, an MRF (magnetic resonance imaging) system used in this embodiment is outlined in FIG. 1.

The MRI system comprises a patient couch on which a patient P lies down, static field generating components for generating a static magnetic field, gradient generating components for appending positional information to a static magnetic field, transmitting/receiving components for transmitting and receiving radio-frequency signals, controlling and calculating components responsible for control of the whole system and reconstruction of images, electrocardiographing components for acquiring an ECG signal which is a representative signal indicative of the cardiac temporal phase of a patient, and breath-hold instructing components for instructing the patient to hold his or her breath. In place of the electrocardiographing components, peripheral components measuring the pulse wave of a patient can be placed.

The static field generating components includes a magnet 1 that is of, for example, a superconducting type, and a static power supply 2 for supplying a current to the magnet 1, and generates a static magnetic field $H_0$ in an axial direction (Z-axis direction) in a cylindrical bore (diagnostic space) into which a patient P is inserted. The magnet unit is provided with shim coils 14. A current used to homogenize a static magnetic field is supplied from a shim coil power supply 15 to the shim coils 14 under the control of a host computer to be described later. The couch top of the patient couch on which the patient P lies down can be inserted into the bore of the magnet 1 so that the couch top can be withdrawn therefrom.

The gradient generating components has a gradient coil unit 3 incorporated in the magnet 1. The gradient coil unit 3 comprises three pairs (kinds) of x-, y-, and z-coils $3x$ to $3z$ used to generate gradients (magnetic field gradients) changing in strength in predetermined physical X-axis, Y-axis, and Z-axis directions that are mutually orthogonal. The gradient generating components further include a gradient power supply 4 for supplying pulsed currents to the x-, y-, and z-coils $3x$ to $3z$ to generate pulsed gradients under the control of a sequencer 5 that will be described later.

The pulses currents supplied from the gradient power supply 4 to the x-, y-, and z-coils $3x$ to $3z$ are controlled, whereby gradients in the three physical X-, Y-, and Z-directions are synthesized arbitrarily. Thus, logical axial directions consisting of directions of a slice gradient $G_s$, a phase-encoding gradient $G_e$, and a readout (frequency-encoding) gradient $G_r$ can be specified and changed arbitrarily. The gradients to be applied individually in the slice direction, phase-encoding direction, and readout direction are superposed on the static magnetic field $H_0$.

The transmitting/receiving components comprises not merely an RF coil 7 located in the vicinity of a patient P in the bore inside the magnet 1 but also a transmitter 8T and a receiver 8R both connected to the coil 7, which operate under the control of a sequencer 5 described later. The transmitter 8T supplies to the RF coil 7 pulsed RF currents of a Larmor frequency to excite spins to cause nuclear magnetic resonance (NMR). The receiver 8R accepts MR signals (RF signals) that the RF coil 7 has received, carries out various kinds of signal processing with the MR signals, such as pre-amplification, intermediate frequency conversion, phase detection, lower-frequency amplification, and specified types of filtering, and A/D-converts the processed MR signals with produced digital data (original raw data).

The control and calculation components includes a sequencer 5 (frequently referred to as a sequence controller), a host computer 6, a calculator 10, a storage 11, a display 12, an input device 13, and a voice generator. Of these, the host computer 6 has the function of providing the sequencer 5 information on a pulse sequence and managing the operations of the entire system according to previously installed software programs.

Figure 2:
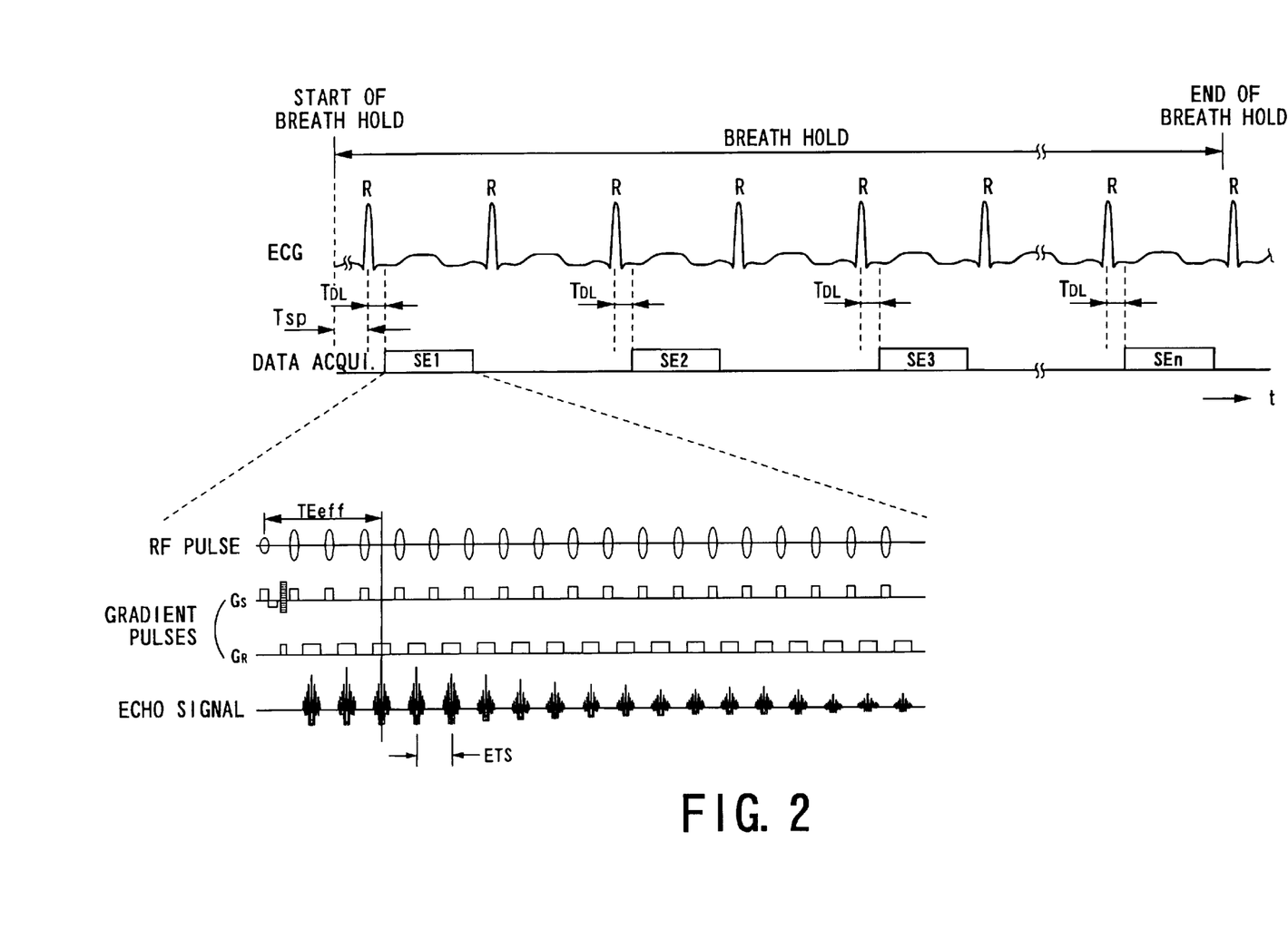
FIG. 2 is a timing chart showing an outlined pulse sequence of an imaging scan.

The host computer 6, which has a CPU and incorporated memories, executes not-shown preparation operations such as scanning for location, before an imaging scan involving a pulse sequence shown in FIG. 2. The imaging scan is an MR scan for acquiring sets of echo data necessary for image reconstruction, and in this embodiment, is selected as a three-dimensional imaging scan. This imaging scan also accompany a breath-holding technique requesting that a patient stops breathing and an ECG (electrocardiograph) gating technique on an ECG signal. On the contrary, the breath-holding and/or ECG gating techniques may be omitted depending on situations.

The pulse sequence is prepared for three-dimensional (3D) or two-dimensional (2D) scans and its pulse train mode based on, for instance, a SE (Spin Echo) method, FSE (Fast SE) method, FASE (Fast Asymmetric SE) method (i.e., an imaging technique which combines a half-Fourier technique with the FSE method), EPI (Echo Planar Imaging) method, and fast recovery (FR) method, Particularly, the FASE and FSE methods are preferable, because of their high resistance to susceptibility and others.

The sequencer 5, which has a CPU and memories, stores pulse sequence information sent from the host computer 6, and controls the operations performed by the gradient power supply 4, transmitter 8T, and receiver 8R according to the stored information. Additionally the sequencer 5 temporarily receives digital data corresponding to MR signals outputted from the receiver 8R, before transferring them to the calculator 10. The pulse sequence information is made up of all information required for operating the gradient power supply 4, transmitter 8T, and receiver 8R according to a series of pulses consisting of a pulse sequence. This pulse sequence information therefore includes information on the strength, duration, and application timing of pulsed currents applied to the x-, y-, and z-coil $3x$ to $3z$.

The calculator 10 receives digital data sent from the receiver 8R via the sequencer 5, maps the received data in a Fourier space (known as a k-space or frequency space) formed in its incorporated memory, and performs a two-dimensional or three-dimensional Fourier transform with the mapped data so as to reconstruct an image in the real space. Moreover, the calculator 10 also carries out such processing as synthesis and difference calculation of image data.

The synthesis processing includes addition processing for image data of a plurality of frames pixel by pixel and maximum intensity projection (MIP) processing which selects a maximum from pixel values aligned along each viewing line direction through three-dimensional data. Alternatively, available is a method that synthesizes the original raw data of a plurality of frames into a frame of original raw data with the frame axes matched in the Fourier space. In addition, the addition includes simple addition, averaging, or weighted addition.

The storage 11 has a memory that can preserve not only reconstructed image data but also image data that have underwent the synthesis and difference calculation. The storage unit has a computer-readable storage medium (not shown), such as a memory or disk, into which a desire type of pulse sequence for this MR imaging is recorded in the form of programs. This storage medium memorizes information about a pulse sequence according to the principle of the present invention.

The display 12 displays an image. The input device 13 is used by an operator to provide the host computer 6 with desired imaging conditions, a pulse sequence, and information about image synthesis and/or difference calculation.

Further, the breath-hold instructing components has a voice generator 16 as one constituent. When receiving a command from the host computer 6, the voice generator 16 utters voice or messages or sound which requests the start or end of patient's breath hold.

Moreover, the electrocardiographing components comprises an ECG sensor 11 attached to the patient body to detect an electric ECG signal and an ECG unit 18 performing various processes including digitization with the detected ECG signal, so that the processed ECG signal is sent to both the host computer 6 and the sequencer 5. This ECG signal is used, for example, by the sequencer 5 to perform an ECG-gating (electrocardiographing synchronization) imaging scan. This enables an appropriate determination of synchronous timing on the ECG-gating technique, whereby an imaging scan on the ECG-gating technique can be performed well to acquire data.

In such configuration, the magnet 1, static power supply 2, gradient coil unit 3, gradient power supply 4, sequencer 5, host computer 6, RF coil 7, and transmitter 8T functionally compose a main part of scaning means, (i.e., scanning unit). The receiver 8R, storage 11, and calculator 10 functionally compose of a main part of data processing means (i.e., data, processing unit). Further, the voice generator 16 and host computer 6 functionally composes a main part of an instructing unit. Still further, the ECG sensor 17 and ECG unit 18 compose a main part of ECG-gating means (i.e., ECG-gating unit). The calculator 10 and storage 11 functionally compose a main part of producing means (i.e., producing unit).

Referring to FIGS. 2 to 7, the operation for the imaging scan performed by the MRI system of the present embodiment will now be described.

Figure 3:
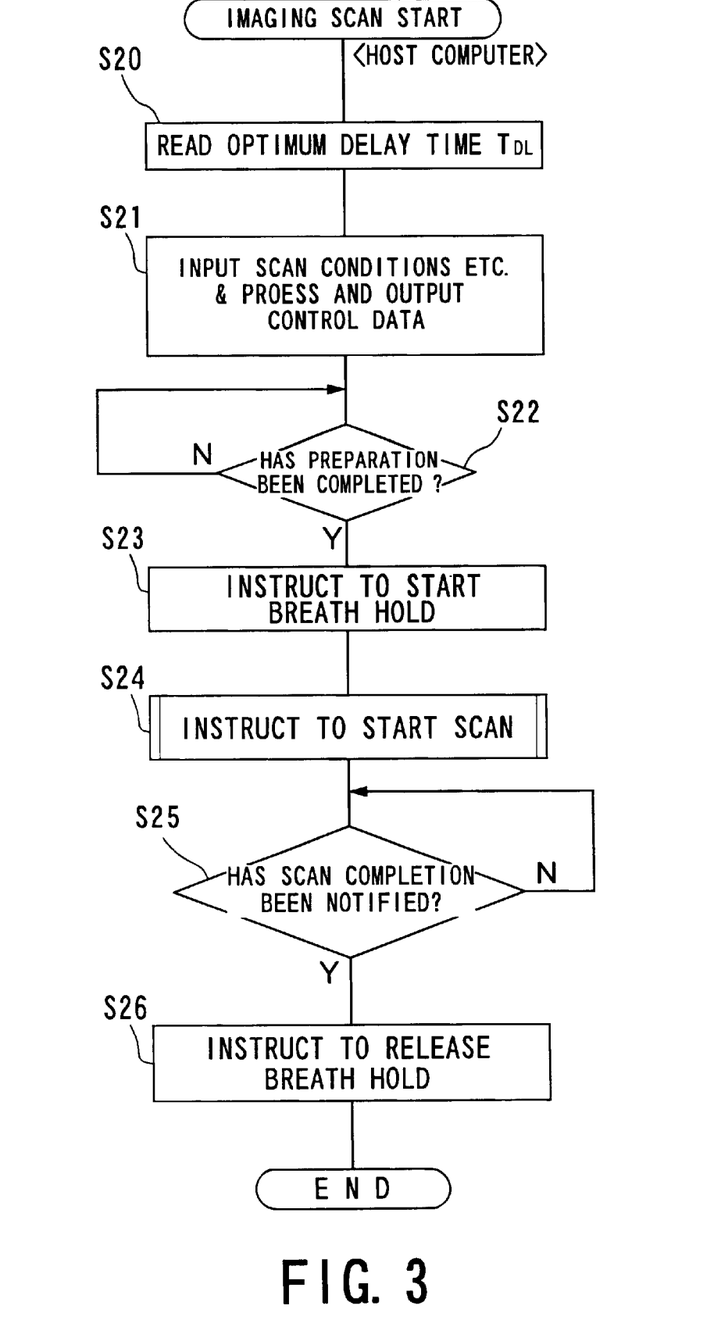
FIG. 3 is an outlined flowchart exemplifying procedures of the imaging scan executed by the host computer.

The host computer 6 executes a not-shown predetermined main program, during which time an imaging scan is executed on, by way of example, a three-dimensional FASE (Fast Asymmetric SE) method, as shown in FIGS. 2 and 3, together with the breath-holding and ECG-gating techniques.

Specifically, first, the host computer 6 reads from, for example, the input device 13 an optimum delay time $T_{CL}$ for ECG-gating determined in an appropriate manner beforehand (step S20). Then, the host computer 6 inputs not only information about scanning conditions (i.e., concerning a 3D-FASE pulse sequence, a phase-encoding direction, an echo train spacing (ETS), an interval between scans each of which is performed on each slice-encoding amount, a matrix size, an effective echo time $TE_{eff}$, and others) but also information about an image processing technique (addition, MIP processing, or others), processes those bits of information including the delay time $T_{DL}$ into control data, and outputs the control data to both the sequencer 5 and calculator 10 (step S21).

In this embodiment, an object to be imaged is the thoracic duct (lymphatic vessels). Through the above scanning conditions, a pulse sequence on the "3D FASE method" is designated, wherein an effective echo time $TE_{eff}=240$ msec and an echo train spacing ETS=5 msec are selected, for example. The lymph liquid flows through the thoracic duct at slower speeds than its surrounding blood and is thinner than its surrounding blood vessels. Considering this fact, the effective echo time is made to agree to a value that is longer than the T1 and T2 MR relaxation times for blood. It is particularly effective when the effective echo time is larger than the T2 relaxation time, resulting in acquisition of a higher-intensity signal of lymph liquid.

Further owing to the fact that the thoracic duct and main blood vessels in the thoracic part run substantially along the patient's body-axis direction, the phase-encoding direction is selected so that it coincides with the superior-inferior direction of a patient. This makes it possible to improve spatial resolution of signals in the phase-encoding direction. This technique has already been disclosed by a paper of "Miyazaki M. et al., A novel MR angiography technique: SPEED acquisition using half-Fourier RARE, J. Magn. Reson. Imaging 1998; 8: 505–507."

If it is determined that an instruction indicating the completion of scan preparations has been issued (step S22), a command indicating the start of breath hold is output to the voice generator 14 (step S23). This causes the voice generator 14 to utter a voice message saying "Please inhale filly and hold your breathing." In response to this message, the patient is forced to hold breathing after a full inhalation.

Figure 4:
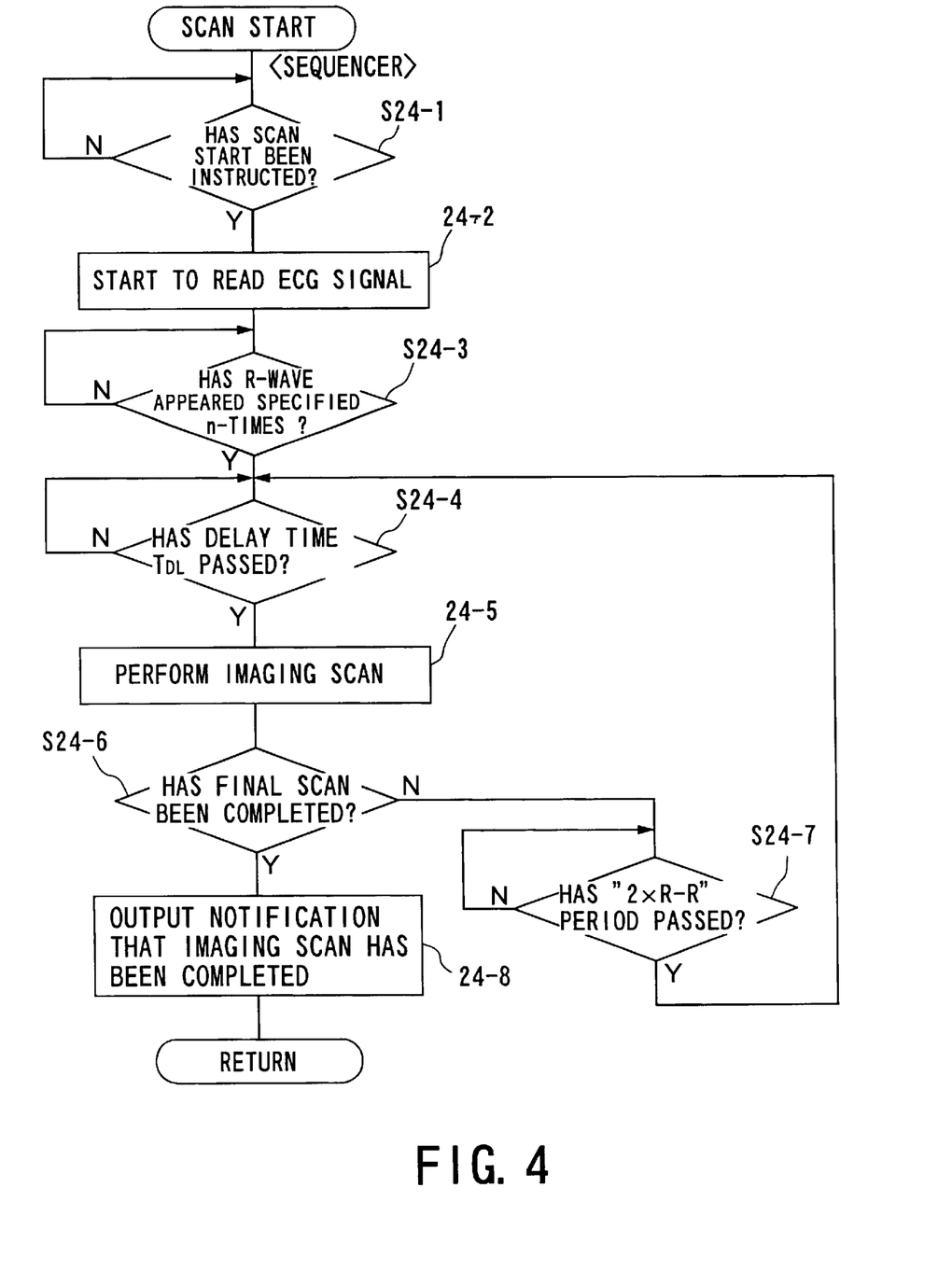
FIG. 4 is an outlined flowchart exemplifying procedures of the imaging scan in which an ECG gating technique executed by the sequencer is used.
Figure 5:
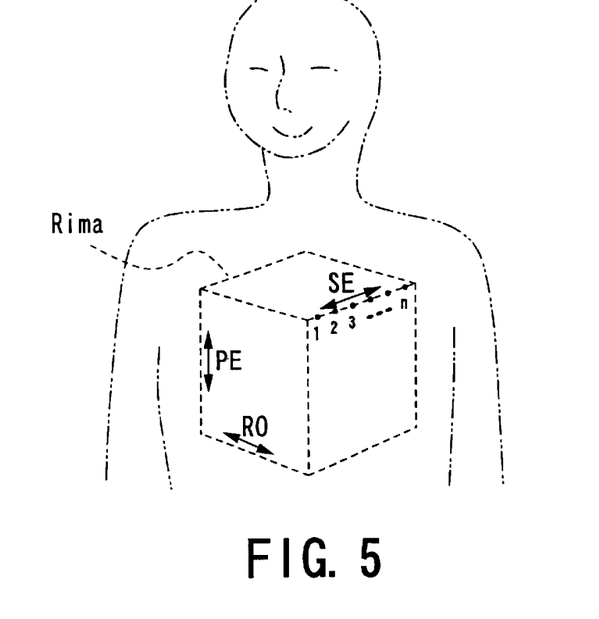
FIG. 5 illustrates a three-dimensional imaging region accompanying gradient directions.

After this, the host computer 6 instructs the sequencer 5 to start the imaging scan (step S24; refer to FIG. 4).

As shown in FIG. 4, on receiving an instruction to start the imaging scan (step S24-1), the sequencer 5 begins reading the ECG signal (step S24-2), and determines whether the R-wave (reference wave) peak of the ECG signal has appeared a specified n-times, on the basis of an ECG trigger signal made synchronous with the peak (step S24-3). The reason to wait for the appearance of the R-wave n-times (for example two times) is to assure the patient's steady breath holding. An adjusting time $T_{sp}$ is set as shown in FIG. 2 to wait for the appearance of the n-th R-wave.

When the specified n-th R-wave has appeared, processing to wait for the determined delay time $T_{DL}$ is performed (step S24-4). The delay time $T_{DL}$ is, as explained before, optimized such that, for imaging lymph liquid, echo-signal intensities become the highest and their depiction performance of an entity become superior. By way of example, the delay time $T_{DL}$ may be selected in the range of 200 to 500 msec.

Regarding as an optimum ECG synchronous timing a time instant when this optimum delay time $T_{DL}$ has passed, the sequencer 5 begins to perform the imaging scan (step S24-5). Practically, the transmitter 8T and the gradient power supply 4 are driven on the pulse sequence information memorized before, so that the first assigned scan is performed with the ECG gating as shown in FIG. 2 according to, for example, a three-dimensional FASE method pulse sequence. In FIG. 2, the phase-encoding directional gradient $G_e$ is omitted from drawing.

Thus, under the first slice-encoding amount SE1 (refer to FIG. 5), echo signals are acquired from a three-dimensional imaging region $R_{ima}$ of the thoracic part set such that it contains the thoracic duct, during a scan time of nearly 600 msec, through the RF coil 7, and sent to the receiver 8R.

On having completed the first imaging scan based on the first slice encoding amount SE1, the sequencer 5 determines if the final imaging scan based on the final slice encoding amount SEn has been completed or not (step S24-6). In the case of NO at this determination (the final imaging scan has not been completed yet), with monitoring the ECG signal, waiting is done until a short period (for example, 2 heartbeats (2R-R) from the R-wave used in the imaging scan) passes (step S24-7). Namely this waiting period defines a repetition time TR.

In this way, after waiting a period corresponding to, for example, 2R-R, when the third R-wave appears (YES at step S24-7), the sequencer 5 returns its processing to the foregoing step S24-4. Hence, at a time instant when the specified delay time $T_{DL}$ has passed since the generation of the ECG signal synchronous with the third R-wave peak, the second imaging scan is commenced in the same way as the above under the next slice-encoding amount SE2, thus echo signals are acquired from the three-dimensional imaging region $R_{ima}$ (steps S24-4, 5). Likewise, echo signals repetitively are acquired until the final slice-encoding amount SEn (for example n=8).

On having completed the final imaging scan under the slice-encoding amount SEn, the determination at step S24-6 becomes YES, thus a notification of the completion of the imaging scan is sent from the sequencer 5 to the host computer 6 (step S24-8). Accordingly the processing is returned to the host computer 6.

When receiving the notification of the completion of the imaging scan from the sequencer 5 (step S25), the host computer outputs a command to release the breath hold to the voice generator 16 (step S26). The voice generator 16 then utters a voice message saying, for example, "You can breathe." toward the patient to terminate the breath holding period (refer to FIG. 2).

Therefore, as pictorially shown by the timing chart in FIG. 2, the imaging scan based on the ECG gating and the breath holding is repetitively performed for each slice encoding n-times (e.g., n=8), every 2R-R, using the 3D-FASE method, for example. The time necessary for scanning of n-times, which corresponds to an interval to impose breath holding on a patient, depends on specified scanning conditions, and it is, for example, approximately 20 to 25 sec. If such interval becomes relatively long, an intermittent breath-holding technique can be adopted for one time of continuous breath holding.

Echo signals emanated from the patient P are received by the RF coil 7, then sent to the receiver 8R, during the scan. The receiver 8R processes the echo signals with various kinds of preprocessing, converting them into digital echo data. The digital echo data are sent via to the sequencer 5 to the calculator 10, where they are mapped in a three-dimensional k-space in digital memory. Because the half-Fourier transform method has been adopted, data that have not been actually acquired in the k-space are obtained by means of calculation, and the calculated data are mapped into the remaining areas of k-space. By such means, the entire k-space may be loaded with echo data.

Figure 6:
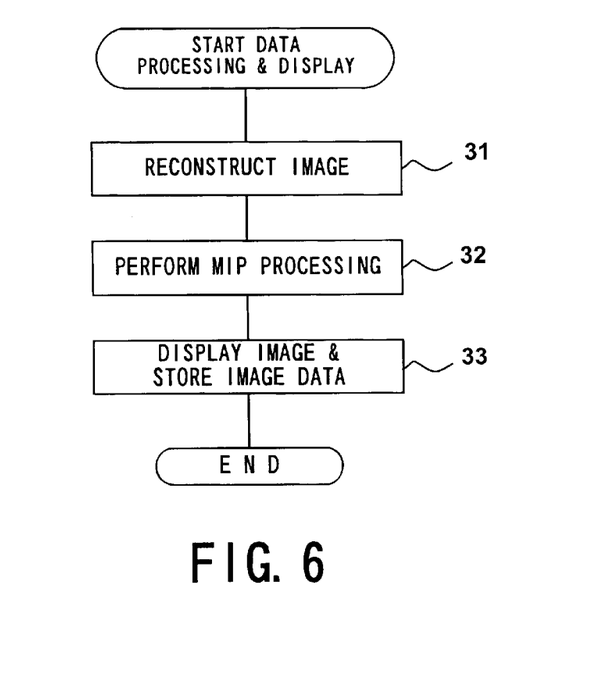
FIG. 6 shows an outlined flowchart of processing procedures of a calculator.

In response to the completion of echo data acquisition through the imaging scans, the host computer 6 commands the calculator 10 to perform data processing and displaying processing. One such example is shown in FIG. 6.

Firstly, the calculator 10 performs a three-dimensional Fourier transform with the echo data in the k-space acquired and mapped through the imaging scans, with the result that real-space image data are reconstructed (step 31). Then this set of three-dimensional image data undergoes MIP processing directed along a desired viewing line direction (step 32). Then the calculator 10 operates to visualize the processed MIP image on the display 12 (step 33).

Figure 7:
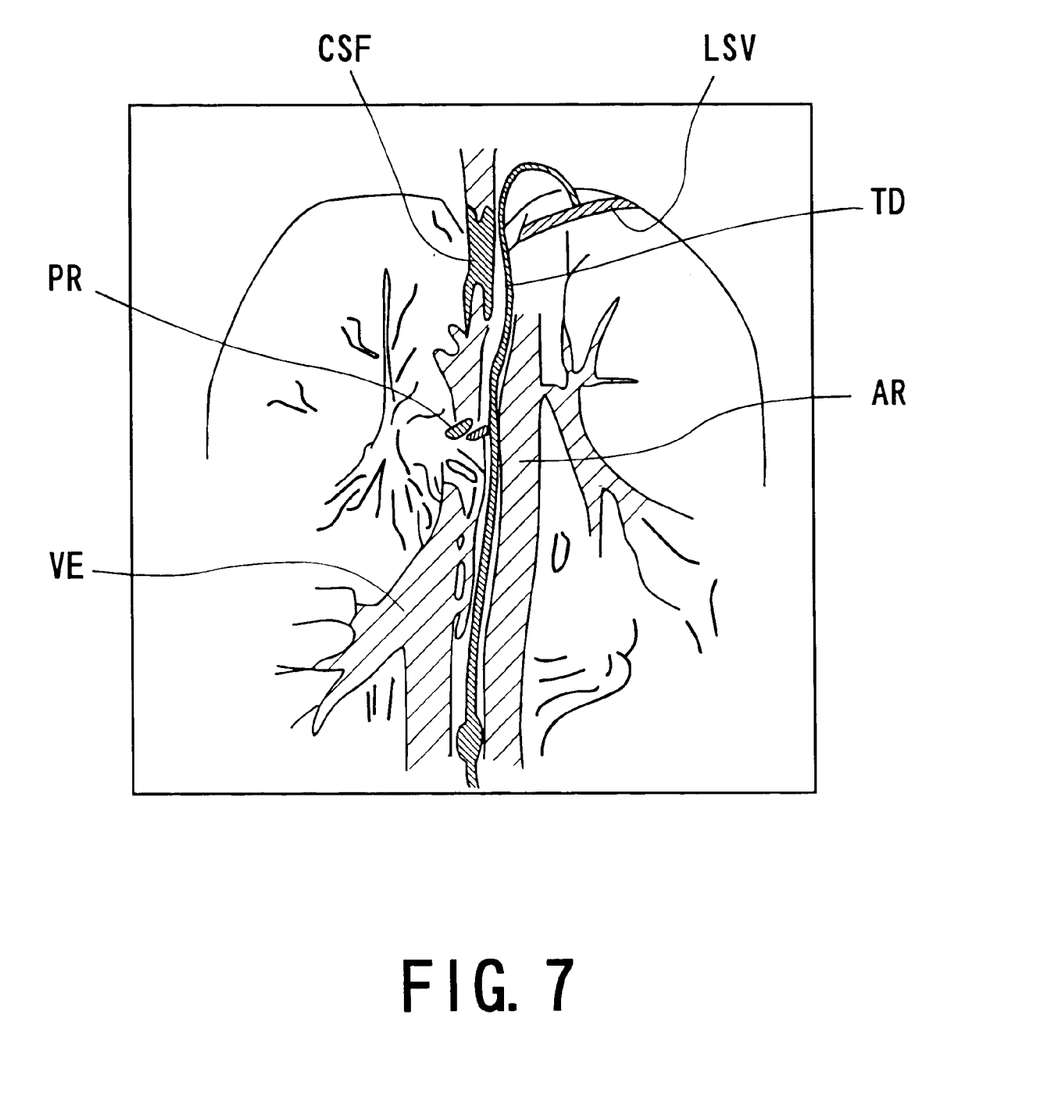
FIG. 7 is a pictorial coronal image sketched by hand from a thoracic duct image actually taken through inventor's experiment conducted under the principle of the present invention.

FIG. 7 shows a coronal image of the thoracic part, which is sketched by hand from a picture actually imaged on the basis of the principle of the present invention. The coronal image is obtained in the coronal direction with its imaging position selected along the thoracic duct, so that the total imaging time can be shortened noticeably. Imaging conditions are based on a three-dimensional FASE method and use both ECG-gating and intermittent breath-holding techniques. Primary imaging parameters are repetition time TR of 5000 msec, effective echo time $TE_{eff}$ of 240 msec, echo train spacing ETS of 5 msec, matrix size of 256×256, 36 slice partitions having a slice thickness of 1.4 mm, the number of averaging ties=one, and FOV of 360 mm×360 mm. The static magnet was 1.5 T in strength. The total data acquisition time was approx. 5 minutes. In order to gain a constant blood depiction performance, a delay time from the R-wave for the ECG-gating is made to be the same for each slice encoding. This delay time $T_{DL}$ was selected as 450 msec (for a volunteer of which R.R wave interval is nearly 900 msec.).

As a result, as shown in the illustration in FIG. 7, the thin thoracic duct (lymphatic vessel) TD running along the thoracic aorta AR and drained into the left subclavian vain LSV in the thoracic part was depicted in higher intensities (in the actual image, the thoracic duct TD brightens in white, whereas in FIG. 7, it is shown by denser hatching lines.). The CSF (cerebrospinal fluid) and peripheral recesses PR were also depicted in higher intensities. The aorta AR and vein (VE) surrounding the thoracic duct TD are also depicted to some extent, but their intensities (luminance levels) are positively suppressed to a lower level to be shown in intermediate gray scales (in FIG. 7, they are illustrated by thinner hatching lines.).

To inventor's knowledge, this is the first report that MR lymphography with a short echo spacing, 3D, half-Fourier, fast spin echo sequence can be used to visualize the thoracic duct without use of a contrast agent.

Thus, making the imaging conditions to agree with those in depicting the lymph liquid, in particular, in terms of the effective echo time $TE_{eff}$ that is thought to be longer than the relaxation times of blood permits the lymph liquid to be depicted in higher signal intensities.

Additionally, because the pulse sequence of which echo train spacing ETS is short is used, blood vessels that provide the background of the thoracic duct can also be depicted to a certain extent and shown in an appropriate gray scale. That is, in addition to the fact that the thoracic duct (lymph liquid) can be depicted steadily, blood vessels also appear in images of the thoracic duct at lower signal levels. This makes it extremely easy to understand the spatial positional relationship of the thoracic duct (lymph vessels) in the images. Hence it is possible to provide MR images that are useful for diagnosing lymphatic-system diseases.

The advantages inherent to this embodiment are as follows.

First, since any contrast agent is not injected, noninvasive imaging can be maintained, greatly relieving physical and mental burdens on patients. At the same time, troublesome operations specific to the contrast technique, such as that it is required to measure timing of contrast effects, can be eliminated. Differently from the contrast technique, repetitively performed imaging is easy to perform.

Because the ECG gating technique is used, motion artifacts caused by the motions of the heart can almost be removed. Further, the breath hold technique is also used, reducing motion artifacts of images in this aspect.

Moreover, in the above embodiment, the echo train spacing ETS of the FASE pulse sequence is not absolutely restricted to 5 msec, but it is desired that the echo train spacing be as short as possible, because it is advantageous in grasping the positional relationship that blood vessel systems providing the background are also depicted in certain signal intensities. For instance, if the echo train spacing falls in a range of 3 to 10 msec, its effects can be realized fully. Using a shorter echo train spacing is also advantageous in shortening the data acquisition time. On one hand, it is not the case that the effective echo time is always 240 msec, while an appropriately selected effective echo time from a range, for example, of 120 to 800 msec, provided the lymph liquid is acquired in higher signal intensities and surrounding blood vessels is acquired in lower signal intensities.

Additionally in the foregoing pulse sequence of the embodiment, it is also preferable to apply one or more pulses for suppressing echo signals emanated from fat.

Furthermore, an objective region to which the present invention can be applied is not limited to the lymphatic vessels, but the lymph nodes are possible to be imaged similarly. Alternatively, the present invention may be applied to liquid existing in recesses of an object. For example, the peripheral recess can be depicted based on the present invention on condition that the effective echo time of a pulse sequence is made to agree to that suitable to depicting the peripheral recess.

The present invention is not restricted to the constructions shown in the foregoing embodiments, but a person having ordinary skin in the art can create a variety of constructions adequately altered or deformed within the scope of the claims.

I claim:

1. An MRI system for imaging flows of blood and a fluid other than blood in a subject to be examined, the system comprising:

ECG-gating means for detecting an ECG signal of the subject;

scanning means for scanning, at a constant cardiac phase determined based on the ECG signal, the subject with a pulse sequence formed to generate a plurality of echoes with different phase-encodes in response to a single shot of magnetic excitation, using an effective echo time selected to depict the flow of fluid higher in echo signal intensity than the flow of blood, using a short echo train spacing thus also allowing the flow of blood to be depicted, and to repeat such scanning so as to acquire three-dimensional echo data;

data processing means for processing the MR signals generated in response to the performance of the pulse sequence into three-dimensional echo data; and producing means for producing from the three-dimensional echo data an image wherein the flow of blood and fluid other than blood are depicted.

2. An MR imaging method for imaging flows of blood and a fluid other than blood in a subject to be examined, the method comprising:

scanning, at a constant cardiac phase as determined by an ECG signal of the subject with a pulse sequence formed to generate a plurality of echoes with different phase-encodes in response to a single shot of magnetic excitation, using an effective echo time selected to depict the flow of fluid higher in echo signal intensity than blood, using a shorter echo train spacing (ETS) thus also allowing the flow of blood to be depicted, and repeating such scanning to acquire three-dimensional echo data;

processing the MR signals generated in response to the pulse sequence into the three-dimensional echo data; and producing from the three-dimensional echo data an image wherein the flow of blood and a fluid other than blood are depicted.

3. The MR imaging method of 2, wherein the flow of fluid other than blood includes a flow of lymph liquid in a lymphatic vessel moving more slowly than the flow of blood.

4. The MR imaging method of 2, wherein the effective echo time is set to be longer than the T1 (spin-lattice relaxation) time of blood.

5. The MR imaging method of 2, wherein the effective echo time $TE_{eff}$ is selected from a range of 120 to 800 msec and the echo train spacing ETS is selected from a range of 3 to 10 msec.

6. The MR imaging method of 2, wherein the constant cardiac phase is delayed by a predetermined interval of time from a heartbeat of the subject, the predetermined interval of time being selected from a range of 500 to 600 msec so as to acquire the echo at a timing falling in a diastole of a heartbeat of the subject.

7. An MRI system for imaging the flows of blood and a fluid other than blood in a subject to be examined, the system comprising:

an ECG-gating unit configured to detect an ECG (electrocardiograph) signal of the subject;

a scanning unit configured to scan the subject, at a constant cardiac phase determined by the ECG signal, in response to a reference signal with a pulse sequence formed to generate a plurality of echoes with different phase encodes in response to a single shot of magnetic excitation, using an effective echo time ($TE_{eff}$) selected to depict the flow of fluid higher in echo signal intensity than blood, using a shorter echo train spacing (ETS) thus also allowing the flow of blood to be depicted, and repeating such scanning to acquire three-dimensional echo data;

a data processing unit configured to process MR signals generated in response to the pulse sequence into the three-dimensional echo data; and a producing unit configured to produce from the three-dimensional echo data an image wherein the flow of both blood and a fluid other than blood are depicted.

8. The MRI system of claim 7, wherein the flow of fluid other than blood includes a flow of lymph liquid existing in a lymphatic vessel and moving at a slower speed than the flow of blood.

9. The MRI system of claim 8, wherein the effective echo time is set to be longer compared to a T1 (spin-lattice relaxation ) time of blood.

10. The MRI system of claim 9, wherein the pulse sequence is either a two-dimensional sequence carried out on a multislice technique or a three-dimensional sequence.

11. The MRI system of claim 10, wherein the pulse sequence is based on any method selected from the group consisting of (a) an FSE (fast SE) method, (b) an FASE method.

12. The MRI system of claim 10, wherein the pulse sequence is based on an FASE (Fast Asymmetric SE) method (wherein echo train spacing (ETS) is selected into short time].

13. The MRI system of claim 10, wherein
the producing unit is configured to include means for obtaining a maximum intensity image as the image.

14. The MRI system of claim 7, wherein the effective echo time $TE_{eff}$ is selected from a range of 120 to 800 msec and the echo train spacing ETS is selected from a range of 3 to 10 msec.

15. The MRI system of claim 7, wherein the constant cardiac phase is delayed by a predetermined interval of time from a heartbeat of the object.

16. The MRI system of claim 15 wherein the predetermined interval of time is selected from a range of 500 to 600 msec so as to acquire the echo at a time falling in a diastole of a heart beat of the subject.

17. The MRI system of claim 7, further comprising an instructing unit configured to instruct the subject to hold a breath during the time in which the pulse sequence is performed by the scanning unit.

18. The MRI system of claim 17, wherein the breath holding is instructed by the instructing unit based on an intermittent breath-holding method.

19. The MRI system of claim 7, wherein the fluid other than blood is liquid filled in a concavity within the object.

20. A non-invasive method of MR lymphography without use of a contrast agent, said method comprising:
using an ECG-gated MRI pulse sequence to provide an enhanced image of lymphatic vessel or node structures while also simultaneously retaining a non-enhanced background image of related blood vessel structures, wherein said ECG-gated MRI pulse sequence using an effective pulse echo first time period chosen to enhance MR signals emanating from said lymphatic vessel or node structures; and said ECG-gated MRI pulse sequences also using echo trains spaced apart by a second time period, substantially shorter than said first time period, to simultaneously maintain recognizable MR signals emanating from said blood vessel structures.

* * * * *